United States Patent
Xi et al.

(10) Patent No.: US 10,301,674 B2
(45) Date of Patent: May 28, 2019

(54) POLYMERASE ASSAY WITH A FRET SUBSTRATE

(75) Inventors: Lei Xi, Foster City, CA (US); Keith P. Bjornson, Union City, CA (US); Stephen P. Hendricks, Los Gatos, CA (US)

(73) Assignee: Life Technologies Corporation, Carlsbad, CA (US)

( * ) Notice: Subject to any disclaimer, the term of this patent is extended or adjusted under 35 U.S.C. 154(b) by 968 days.

(21) Appl. No.: 13/213,427

(22) Filed: Aug. 19, 2011

(65) Prior Publication Data

US 2012/0070838 A1    Mar. 22, 2012

Related U.S. Application Data

(60) Provisional application No. 61/375,310, filed on Aug. 20, 2010.

(51) Int. Cl.
   *C12Q 1/686* (2018.01)
   *C12Q 1/6853* (2018.01)

(52) U.S. Cl.
   CPC .......... *C12Q 1/686* (2013.01); *C12Q 1/6853* (2013.01)

(58) Field of Classification Search
   None
   See application file for complete search history.

(56) References Cited

U.S. PATENT DOCUMENTS

| 5,866,336 A | 2/1999 | Nazarenko et al. |
| 6,020,130 A * | 2/2000 | Gold et al. ............... 435/5 |
| 6,967,075 B2 * | 11/2005 | Zhong et al. ............. 435/5 |
| 7,537,886 B1 * | 5/2009 | Nazarenko et al. ....... 435/6.12 |

FOREIGN PATENT DOCUMENTS

| WO | 1996/010640 | 4/1996 |
| WO | 2001/38587 | 5/2001 |
| WO | 2005/003388 | 1/2005 |
| WO | 2008/063194 | 5/2008 |
| WO | 2010/036359 | 4/2010 |

OTHER PUBLICATIONS

Marras, S.A.E. Methods in Molecular Biology (2006) 335: 3-16.*
Summerer, D. Methods in Molecular Biology (2008) 429: 225-235.*
Biroccio et al. Journal of Virology (2002) 76(8): 3688-3696.*
Dorjsuren, Dorjbal et al., "A Real-Time Fluorescence Method for Enzymatic Characterization of Specialized Human DNA Polymerases", *Nucleic Acids Research*, vol. 37, No. 19, 2009, e128.
Krebs, Joseph F. et al., "Novel FRET-Based Assay to Detect Reverse Transcriptase Activity Using Modified dUTP Analogues", *Bioconjugate Chem.*, vol. 19, No. 1, 2008, 185-191.
Ma, Changbei "Real-Time Monitoring of DNA Polymerase Activity Using Molecular Beacon", *Analytical Biochemistry*, vol. 353, No. 1, 2006, 141-143.

(Continued)

*Primary Examiner* — Angela M. Bertagna

(57) ABSTRACT

This specification generally relates to non-radioactive methods of detecting nucleic acid polymerase activity and methods of detecting compounds that modulate nucleic acid polymerase activity. The activity may be measured in real-time using a real-time PCR instrument.

22 Claims, 5 Drawing Sheets

Specification includes a Sequence Listing.

(56) References Cited

OTHER PUBLICATIONS

Nazarenko, Irina A. et al., "A Closed Tube Format for Amplification and Detection of DNA Based on Energy Transfer", *Nucleic Acids Research*, vol. 25, No. 12, 1997, 2516-2521.
International Search Report along with the Written Opinion of the ISA for International Application No. PCT/US2011/048503 dated Nov. 29, 2011.
PCT/US2011/048503 ; International Preliminary Report on Patentability dated Feb. 26, 2013.

* cited by examiner

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgtaggactc ggaagtcgac                                                    20

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      template oligonucleotide
<220> FEATURE:
<221> NAME/KEY: misc_feature
<222> LOCATION: (1)..(1)
<223> OTHER INFORMATION: BHQ1 quencher attached
<220> FEATURE:
<221> NAME/KEY: misc_feature
<222> LOCATION: (17)..(17)
<223> OTHER INFORMATION: Fluorophore attached -continued

<400> SEQUENCE: 2
cagcgtgggg tttgcgtcga cttccgagtc ctacg                                35

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      complement oligonucleotide

<400> SEQUENCE: 3
cgtaggactc ggaagtcgac gcaaacccca cgctg                                35

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: Synthetic
      substrate oligonucleotide
<220> FEATURE:
<221> NAME/KEY: misc_feature
<222> LOCATION: (1)..(1)
<223> OTHER INFORMATION: IBK quencher attached
<220> FEATURE:
<221> NAME/KEY: misc_feature
<222> LOCATION: (15)..(15)
<223> OTHER INFORMATION: FAM fluorophore attached

<400> SEQUENCE: 4
atcatatcat caactggccg tcgttttaca tatgtaaaac gacggccagt t              51

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Synthetic
      substrate oligonucleotide
<220> FEATURE:
<221> NAME/KEY: misc_feature
<222> LOCATION: (1)..(1)
<223> OTHER INFORMATION: 56-TAMN quencher attached
<220> FEATURE:
<221> NAME/KEY: misc_feature
<222> LOCATION: (15)..(15)
<223> OTHER INFORMATION: Fluorophore attached

<400> SEQUENCE: 5
atcatatcat caactggccg tcgttttaca tatgtaaaac gacggccagt t              51

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      substrate oligonucleotide

<400> SEQUENCE: 6
atcatatcat caactggccg tcgttttaca tatgtaaaac gacggccagt t              51

<210> SEQ ID NO 7
<211> LENGTH: 50
<212> TYPE: DNA
<213> ORGANISM: Artificial Sequence
<220> FEATURE:

```
<223> OTHER INFORMATION: Description of Artificial Sequence: Synthetic
      substrate oligonucleotide
<220> FEATURE:
<221> NAME/KEY: misc_feature
<222> LOCATION: (1)..(1)
<223> OTHER INFORMATION: IBK quencher attached
<220> FEATURE:
<221> NAME/KEY: misc_feature
<222> LOCATION: (14)..(14)
<223> OTHER INFORMATION: FAM fluorophore attached

<400> SEQUENCE: 7
tcatatcatc cactggccgt cgttttacat atgtaaaacg acggccagtc          50

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      substrate oligonucleotide
<220> FEATURE:
<221> NAME/KEY: misc_feature
<222> LOCATION: (1)..(1)
<223> OTHER INFORMATION: IBK quencher attached
<220> FEATURE:
<221> NAME/KEY: misc_feature
<222> LOCATION: (15)..(15)
<223> OTHER INFORMATION: FAM fluorophore attached
<220> FEATURE:
<221> NAME/KEY: modified_base
<222> LOCATION: (51)..(51)
<223> OTHER INFORMATION: dideoxycytosine (ddC)

<400> SEQUENCE: 8
atcatatcat cgactggccg tcgttttaca tatgtaaaac gacggccagt c         51

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Synthetic
      substrate oligonucleotide
<220> FEATURE:
<221> NAME/KEY: misc_feature
<222> LOCATION: (1)..(1)
<223> OTHER INFORMATION: IBK quencher attached
<220> FEATURE:
<221> NAME/KEY: misc_feature
<222> LOCATION: (15)..(15)
<223> OTHER INFORMATION: FAM fluorophore attached
<220> FEATURE:
<221> NAME/KEY: modified_base
<222> LOCATION: (51)..(51)
<223> OTHER INFORMATION: dideoxycytosine (ddC)

<400> SEQUENCE: 9
atcatatcat ccactggccg tcgttttaca tatgtaaaac gacggccagt c         51

<210> SEQ ID NO 10
<211> LENGTH: 54
<212> TYPE: DNA
<213> ORGANISM: Artificial Sequence
<220> FEATURE:
<223> OTHER INFORMATION: Description of Artificial Sequence: Synthetic
      substrate oligonucleotide
<220> FEATURE:
<223> OTHER INFORMATION: Description of Combined DNA/RNA Molecule:
      Synthetic substrate oligonucleotide
<220> FEATURE:
<221> NAME/KEY: misc_feature
<222> LOCATION: (1)..(1)
```

```
<223> OTHER INFORMATION: BHQ1 quencher attached
<220> FEATURE:
<221> NAME/KEY: misc_feature
<222> LOCATION: (53)..(53)
<223> OTHER INFORMATION: FAM fluorophore attached

<400> SEQUENCE: 10
aucaucauau caucaacugg ccgucguuuu acatatgtaa aacgacggcc agtt          54
```

POLYMERASE ASSAY WITH A FRET SUBSTRATE

CROSS-REFERENCE TO RELATED APPLICATIONS

This application claims the benefit of priority under 35 U.S.C. § 119(e) to U.S. Provisional Application No. 61/375,310 filed Aug. 20, 2010, which is herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jul. 29, 2013, is named LT00287_SL.txt and is 4,057 bytes in size.

FIELD

This specification generally relates to non-radioactive methods of detecting nucleic acid polymerase activity and methods of detecting compounds that modulate nucleic acid polymerase activity.

BACKGROUND

Traditionally, activity assays of polymerases, including DNA-directed DNA polymerases, DNA-directed RNA polymerases, RNA-directed DNA polymerases and RNA-directed RNA polymerases, involve a primed nucleic acid template, $^{32}$P-labeled dNTPs, a polymerase and a buffer system. The quantity of the incorporated radio-isotope labeled dNTPs into the final product is used to measure the activity of the enzyme. This assay method requires skilled experts, specialized facilities for radioisotopes and produces radioisotope-contaminated waste.

Non-radioactive methods that are now available, including the M13/SYBR Green assay, and a real-time assay using a DNA binding dye, DAPI, have the disadvantage of being complicated, involving expensive instruments for monitoring the reactions, lengthy preparation time and a large quantity of reagents.

Therefore, in view of the state of the art, a need exists for broadly applicable assays for the presence or activity of polymerases using a non-radioactive method.

Fluorescence resonance energy transfer (FRET) is a form of molecular energy transfer (MET), a process by which energy is passed non-radioactively between a donor molecule and an acceptor molecule. FRET arises from the properties of certain chemical compounds; when excited by exposure to particular wavelengths of light, they emit light (i.e., they fluoresce) at a different wavelength. Such compounds are termed fluorophores or fluorescent labels. In FRET, energy is passed non-radioactively over a long distance (e.g., 10-100 Angstroms) between a donor molecule, which may be a fluorophore, and an acceptor molecule, which may be a quencher or another fluorophore. The donor absorbs a photon and transfers this energy non-radioactively to the acceptor (Forster, 1949, Z. Naturforsch. A4:321-327; Clegg, 1992, Methods Enzymol. 211:353-388).

When two fluorophores whose excitation and emission spectra overlap are in close proximity, excitation of one fluorophore will cause it to emit light at wavelengths that are absorbed by, and that stimulate, the second fluorophore, causing it in turn to fluoresce. In other words, the excited-state energy of the first (donor) fluorophore is transferred by a resonance induced dipole-dipole interaction to the neighboring second (acceptor) fluorophore. As a result, the lifetime of the donor molecule is decreased and its fluorescence is quenched, while the fluorescence intensity of the acceptor molecule is enhanced and depolarized. When the excited-state energy of the donor is transferred to a non-fluorophore acceptor, the fluorescence of the donor is quenched without subsequent emission of fluorescence by the acceptor. In this case, the acceptor functions as a quencher.

Pairs of molecules that can engage in fluorescence resonance energy transfer (FRET) are termed FRET pairs. In order for energy transfer to occur, the donor and acceptor molecules must typically be in close proximity (e.g., up to 70 to 100 Angstroms) (Clegg, 1992, Methods Enzymol. 211:353-388; Selvin, 1995, Methods Enzymol. 246:300-334). The efficiency of energy transfer falls off rapidly with increased distance between the donor and acceptor molecules. Effectively, this means that FRET can most efficiently occur up to distances of about 70 Angstroms.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches.

SUMMARY

In general, the teachings herein provide methods, compositions and kits for assaying for the presence and activity of one or more polymerases in a sample using non-radioactive methods involving FRET.

Some embodiments include methods of detecting nucleic acid polymerase activity, such methods comprising:

providing a primer-template duplex comprising a nucleic acid template and a nucleic acid primer, wherein the template comprises a single-stranded tail having a 5' end having a first FRET label attached, and wherein the template or the primer comprises a second FRET label attached, wherein one FRET label is a quencher and the other FRET label is a fluorophore;

contacting the duplex with at least one nucleotide triphosphate or analog thereof; and detecting a signal from the fluorophore, wherein a change in the signal compared to a control is indicative of nucleic acid polymerase activity.

In some aspects, the first FRET label is a quencher and the second FRET label is a fluorophore. In some aspects, the first FRET label is a fluorophore and the second FRET label is a quencher. In some aspects, the second FRET label is not located at the 3' end of the primer. The primer and template may be covalently connected or may not be covalently connected. If connected, the primer and template may be covalently connected as a stem loop structure. In some aspects, the second FRET label is attached to the primer. In some aspects, the quencher and fluorophore are separated at a distance such that when the duplex is not polymerized, the fluorophore is quenched by the quencher and when the duplex is polymerized, the quenching is reduced and the fluorescence increases. In some aspects, the distance between the fluorophore and the quencher is between about 4 and 20 bases. In some aspects, the steps in the method provided herein may be performed simultaneously or separately in any order. In some aspects, the quencher is a Black Hole Quencher®, an Iowa Black® quencher, an Eclipse® Dark quencher or a DABCYL quencher. In some aspects, the fluorophore is FAM, TET, HEX, Cy3, TMR, ROX, Texas Red®, LC red 640, Cy5 or LC red 705. If the quencher is a Black Hole Quencher®, an Iowa Black® quencher or an Eclipse® Dark quencher, the distance between the fluorophore and the quencher is about 15 bases. If the quencher is a DABCYL quencher, the distance between the quencher and the fluorophore is about 5 bases. The detection may be performed using a real-time PCR instrument. In some aspects, the polymerase may be a DNA-directed DNA polymerase, a DNA-directed RNA polymerase, an RNA-directed RNA polymerase or an RNA-directed DNA polymerase. In some aspects, the primer-template duplex is a DNA/RNA hybrid duplex.

Some embodiments include substrates for detecting or measuring polymerase activity comprising a primer-template duplex comprising a nucleic acid template and a nucleic acid primer, wherein the template comprises a single-stranded tail having a 5' end having a first FRET label attached, and wherein the template or the primer comprises a second FRET label, wherein one FRET label is a quencher and the other FRET label is a fluorophore. In such methods, the primer and template are complementary to each other. In some aspects, the first FRET label is a quencher and the second FRET label is a fluorophore. In some aspects, the first FRET label is a fluorophore and the second FRET label is a quencher. In some aspects, the second FRET label is not located at the 3' end of the primer. In some aspects, the primer and template are covalently connected. In some aspects, the primer and template are covalently connected as a stem-loop structure. In some aspects, the second FRET label is attached to the primer. In some aspects, the quencher and fluorophore are separated at a distance such that when the duplex is not polymerized, the fluorophore is quenched by the quencher, and when the duplex is polymerized, the quenching is reduced and the fluorescence increases. In some aspects, the distance between the fluorophore and the quencher is between about 4 bases and 20 bases. In some aspects, the distance is between about 3 bases and about 50 bases. In some aspects, the primer-template duplex is a DNA/RNA hybrid primer-template duplex.

Some embodiments provide kits for detecting or measuring polymerase activity comprising:

a primer-template duplex comprising a nucleic acid template and a nucleic acid primer, wherein the template comprises a single-stranded tail having a 5' end having a first FRET label attached, and wherein the template or primer comprises a second FRET label, wherein one FRET label is a quencher and the other FRET label is a fluorophore;

at least one nucleotide triphosphate or analog thereof; and at least one polymerase for use as a control.

Further embodiments provide methods of screening for compounds that modulate nucleic acid polymerase activity, such methods comprising:

providing a primer-template duplex comprising a nucleic acid template and a nucleic acid primer, wherein the template comprises a single-stranded tail having a 5' end having a first FRET label attached, and wherein the template or the primer comprises a second FRET label, wherein one FRET label is a quencher and the other FRET label is a fluorophore;

contacting the duplex with a nucleic acid polymerase;

contacting the duplex with at least one nucleotide triphosphate or analog thereof;

contacting the duplex with a compound; and detecting a signal from the fluorophore, wherein a change in the signal compared to a control is indicative that the compound modulates nucleic acid polymerase activity.

In some aspects, the primer-template duplex is a DNA/RNA primer-template hybrid duplex. In some aspects, the quencher and fluorophore are separated at a distance such that when the duplex is not polymerized, the fluorophore is quenched by the quencher, and when the duplex is polymerized, the quenching is reduced and the fluorescence increases.

Further embodiments provide methods of quantitating nucleic acid polymerase activity, such methods comprising:

providing a substrate comprising a primer-template duplex comprising a nucleic acid template and a nucleic acid primer, wherein the template comprises a single-stranded tail having a 5' end having a first FRET label attached, and wherein the template or the primer comprises a second FRET label, wherein one FRET label is a quencher and the other FRET label is a fluorophore;

contacting the duplex with a nucleic acid polymerase;

contacting the duplex with at least one nucleotide triphosphate or analog thereof;

admixing various concentrations of a standard; and detecting a signal from the fluorophore, wherein a change in the signal compared to a control is indicative of a nucleic acid polymerase activity, wherein the standard comprises a "filled-in" version of the substrate.

In some aspects, the primer and template are not covalently linked. In some aspects, the primer and template are covalently linked. In some aspects, the primer-template duplex is a DNA/RNA primer-template hybrid duplex.

Further embodiments provide methods of quantitating nucleic acid polymerase activity, such methods comprising:

providing a primer-template duplex comprising a nucleic acid template and a nucleic acid primer, wherein the template comprises a single-stranded tail having a 5' end having a first FRET label attached, and wherein the template or the primer comprises a second FRET label, wherein one FRET label is a quencher and the other FRET label is a fluorophore;

contacting the duplex with a nucleic acid polymerase;

contacting the duplex with at least one nucleotide triphosphate or analog thereof;

detecting a signal from the fluorophore; and further comprising providing a standard, the standard comprising the primer-template duplex having a "filled-in" single-stranded tail;

detecting a signal from the fluorophore; and using the signal obtained at different concentrations of the standard and the signal obtained from the primer-template hybrid to quantitated the activity of the enzyme in units.

In some aspects, the first FRET label is a quencher and the second FRET label is a fluorophore. In some aspects, the first FRET label is a fluorophore and the second FRET label is a quencher. In some aspects, the second FRET label is not located at the 3' end of the primer. In some aspects, the primer and template are covalently connected. In some aspects, the primer and template are covalently connected as a stem-loop structure. In some aspects, the second FRET label is attached to the primer. In some aspects, the quencher and fluorophore are separated at a distance such that when the duplex is not polymerized, the fluorophore is quenched by the quencher, and when the duplex is polymerized, the quenching is reduced and the fluorescence increases. In some aspects, the distance between the fluorophore and quencher is between about 3 and 50 bases, including between about 4 and 20 bases. In some aspects, the steps may be performed simultaneously or separately in any order. In some aspects, the quencher is chosen from: a Black Hole Quencher®, an Iowa Black® quencher, an Eclipse® Dark quencher or a DABCYL quencher. In some aspects, the fluorophore is chosen from: FAM, TET, HEX, Cy3, TMR, ROX, Texas Red®, LC red 640, Cy5 and CL red 705. In some aspects, the quencher is a Black Hole Quencher®, an Iowa Black® quencher or an Eclipse® Dark quencher and the distance between the fluorophore and the quencher is about 15 bases. In some aspects, the quencher is a DABCYL quencher and the distance between the fluorophore and the quencher is about 5 bases. In some aspects, the detection is performed using a real-time PCR instrument. In some aspects, the polymerase is chosen from: a DNA-directed DNA polymerase, a DNA-directed RNA polymerase, an RNA-directed RNA polymerase and an RNA-directed DNA polymerase.

Other embodiments include kits for the quantification or detection of one or more polymerases in a sample, including a fluorogenic substrate. The fluorogenic substrate includes a fluorophore and a quencher, such that the quencher and fluorophore are separated at a distance such that when the duplex is not polymerized the fluorophore is quenched by the quencher and when the duplex is polymerized the fluorophore is not quenched by the quencher. In some embodiments, the kit may be used in methods of polymerase activity detection and quantification. In some embodiments, the kit includes a control polymerase. In other embodiments, the kits are used for multiplexed reactions, such as to identify one or more polymerases in a sample.

Any of the above embodiments may be used alone or together with one another in any combination. Inventions encompassed within this specification may also include embodiments that are only partially mentioned or alluded to or are not mentioned or alluded to at all in this brief summary or in the abstract.

BRIEF DESCRIPTION OF THE FIGURES

Although the following figures depict various examples of the invention, the invention is not limited to the examples depicted in the figures.

FIG. 5A shows the enzyme activity vs. rate. FIG. 5B shows the control activity vs. rate. FIG. 5C shows the fluorescence signal (RFU) vs. the concentration of Complement (nM).

DETAILED DESCRIPTION

Figure 1:
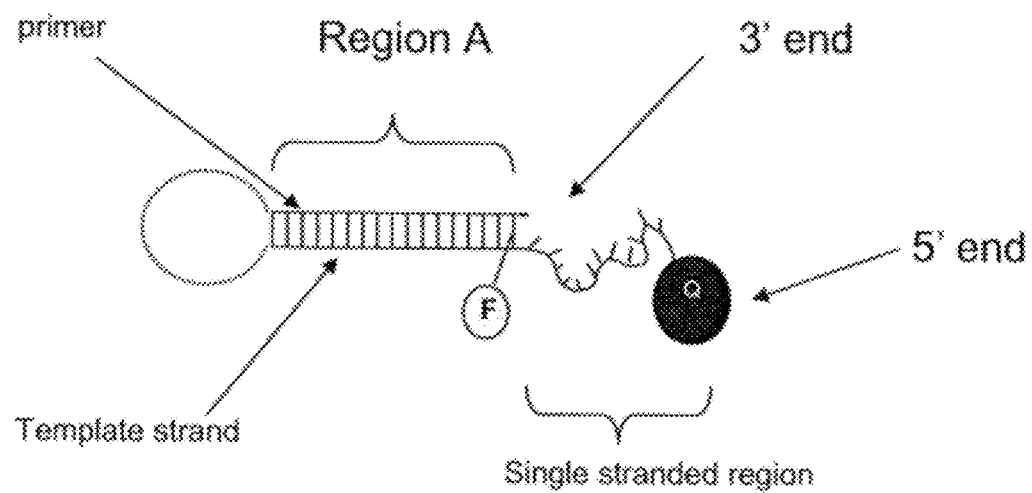
FIG. 1 shows a diagram of an embodiment of the primer-template duplex (FRET substrate) in an unpolymerized state (State I).

Although various embodiments of the invention may have been motivated by various deficiencies with the prior art, which may be discussed or alluded to in one or more places in the specification, the embodiments disclosed herein do not necessarily address any of these deficiencies. In other words, different embodiments disclosed herein may address different deficiencies that may be discussed in the specification. Some embodiments may only partially address some deficiencies or just one deficiency that may be discussed in the specification, and some embodiments may not address any of these deficiencies.

In general, the specification provides methods and compositions for assaying for the presence and activity of one or more polymerases in a sample using non-radioactive methods involving FRET. The methods also have the advantage of using simple fluorogenic substrates. The methods also have the advantage of being real-time polymerase assays and may be monitored using any real-time PCR instrument. The FRET polymerase assays disclosed herein require fewer reagents, have a quicker preparation time, have less dead time, and less read time. In addition, the methods provide the further advantage of being less variable than many of the available non-radioactive methods.

The methods and compositions disclosed herein are partially derived from the identification of a FRET substrate that allows the identification of and quantification of polymerase activity. The FRET substrate is a primer-template duplex having a primer and a template. The template has a 5' single-stranded tail that is labeled with a FRET label. The primer or the template has a second FRET label within the duplex part of the primer-template duplex. The second FRET label is internal to the 3' end of the primer. The second FRET label may be located on the primer or the template but not at the 3' end of the primer. This ensures that extension of the primer into the single-stranded region of the FRET substrate can occur if a polymerase is present. The two FRET labels on the FRET substrate are a quencher and a fluorophore. The quencher and fluorophore are separated at a distance such that when the duplex is not polymerized the fluorophore is quenched by the quencher and when the duplex is polymerized, the fluorophore is not quenched by the quencher. Thus, the specific type of quencher and fluorophore is chosen so that the fluorophore is quenchable by the quencher. The distance between the quencher and fluorophore can be different for different fluorophore-quencher pairs. For example, the distance may be between about 4 and 20 bases, including but not limited to about 5, 6, 7, 8, 9, 10, 11, 12, 13, 14, 15, 16, 17, 18, and 19 bases. This distance may be chosen to provide for the maximum amount of quenching while not being so distant as to provide a high background. Thus, for example, when the quencher is DABCYL the distance from the fluorophore may be about 5 bases.

Definitions and General Methods

The practice of the present invention will employ, unless otherwise indicated, conventional methods of chemistry, biochemistry, molecular biology, virology, immunology and pharmacology, within the skill of the art. Such techniques are explained fully in the literature. In the description that follows, a number of terms used in chemistry, biochemistry, molecular biology, virology, immunology and pharmacology are extensively utilized. In order to provide a clearer and consistent understanding of the specification and claims, including the scope to be given such terms, the following definitions are provided.

As used in this specification and the appended claims, the singular forms "a," "an" and "the" include plural references unless the content clearly dictates otherwise.

As used herein "nucleotide" refers to a base-sugar-phosphate combination. Nucleotides are monomeric units of a nucleic acid sequence (DNA and RNA) and deoxyribonucleotides are "incorporated" into DNA by DNA polymerases. The term nucleotide includes deoxyribonucleoside triphosphates such as dATP, dCTP, dITP, dUTP, dGTP, dTTP, or derivatives thereof. Such derivatives include, for example, [aS]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates (ddNTPs) include, but are not limited to, ddATP, ddCTP, ddGTP, ddITP, ddUTP and ddTTP.

The term "nucleic acid or nucleotide analogs" refers to analogs of nucleic acids made from monomeric nucleotide analog units, and possessing some of the qualities and properties associated with nucleic acids. Nucleotide analogs may have modified (i) nucleobase moieties, e.g. C-5-propyne pyrimidine, pseudo-isocytidine and isoguanosine, (ii) sugar moieties, e.g. 2'-O-alkyl ribonucleotides, or (iii) internucleotide moieties, e.g. 3'-N-phosphoramidate. See Englisch, U. and Gauss, D. "Chemically modified oligonucleotides as probes and inhibitors," Angew. Chem. Int. Ed. Engl. 30:613-29 (1991). A class of analogs where the sugar and internucleotide moieties have been replaced with a 2-aminoethylglycine amide backbone polymer is peptide nucleic acids PNA. See P. Nielsen et al., Science 254:1497-1500 (1991).

As used herein, the terms "hybridization" and "hybridizing" refer to the pairing of two complementary single-stranded nucleic acid molecules (RNA/RNA, RNA/DNA or DNA/DNA) to give a double-stranded molecule. As used herein, two nucleic acid molecules may be hybridized, even if the base pairing is not completely complementary. Accordingly, mismatched bases do not prevent hybridization of two nucleic acid molecules provided that appropriate conditions, well known in the art, are used.

The term "homologous region" refers to a region of nucleic acid with homology to another nucleic acid region. Thus, whether a "homologous region" is present in a nucleic acid molecule is determined with reference to another nucleic acid region in the same or different molecule. Further, since nucleic acid molecules are often double-stranded, the term "homologous region," as used herein refers to the ability of nucleic acid molecules to be capable of hybridizing to each other. As an example, a single-stranded nucleic acid molecule may have two homologous regions which are capable of hybridizing to each other. Thus, the term "homologous region" includes nucleic acid segments with complementary sequences.

The term "complementary" and "complementarity" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementary refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other.

As used herein, the term "primer" refers to a single-stranded oligonucleotide that is extended by covalent bonding of nucleotide monomers during amplification or polymerization of a template molecule.

The term "incorporating" as used herein means becoming a part of a DNA or RNA molecule or primer.

The term "end-point" refers to a method where data collection occurs only once the reaction has been stopped.

The term "real-time" or "real-time continuous" refers to a method where data collection occurs through periodic monitoring during the course of the polymerization reaction.

The term "RNA-dependent polymerase" refers to an enzyme that produces a polynucleotide sequence (DNA or RNA), complementary to a pre-existing template polyribonucleotide (RNA). The RNA-dependent polymerase may be either an RNA-dependent RNA polymerase or an RNA-dependent DNA polymerase. The RNA-dependent polymerase may be either an RNA viral polymerase or replicase or an RNA-dependent cellular polymerase.

The term "DNA-dependent polymerase" refers to an enzyme that produces a polynucleotide sequence (DNA or RNA), complementary to a pre-existing template polydeoxyribonucleotide (DNA). The DNA-dependent polymerase may be either a DNA-dependent RNA polymerase or a DNA-dependent DNA polymerase.

The term "cellular polymerase" refers to a polymerase derived from a cell. The cell may be prokaryotic or eukaryotic. The term "mammalian RNA polymerase II" refers to an RNA polymerase II derived from a mammal. The polymerase is optionally naturally occurring, or artificially (e.g., recombinantly) produced. A "human RNA polymerase II" is an RNA polymerase II derived from a human. The polymerase is optionally naturally occurring, or artificially (e.g., recombinantly) produced. A "murine RNA polymerase II" is an RNA polymerase II derived from a mouse. The polymerase is optionally naturally occurring, or artificially (e.g., recombinantly) produced.

As used herein, the terms "polymerization" and "extension" refer to the act of catalyzing the linking of nucleotide triphosphates in a specific order, using single-stranded nucleic acids as a template. Polymerization or extension do not require complete polymerization of the template, but only 3 or more nucleotides need be added for polymerization to occur.

The terms "nucleic acid," "polynucleotide," "oligonucleotide" and "oligo" refer to polymers of nucleotide monomers or analogs thereof, including double- and single-stranded deoxyribonucleotides, ribonucleotides, alpha-anomeric forms thereof, and the like. Usually, the monomers are linked by phosphodiester linkages, where the term "phosphodiester linkage" refers to phosphodiester bonds or bonds including phosphate or analogs thereof, including associated counterions, e.g., $H^+$, $NH_4^+$ and $Na^+$.

The term "nucleotide triphosphate or analog thereof" refers to combinations of one or more ribonucleotide triphosphates (GTP, UTP, CTP and ATP or nucleotide analogs thereof), or deoxyribonucleotide triphosphates (dATP, dGTP, dTTP, dCTP or deoxyribonucleotide analogs thereof); adenosine 5'-phosphosulfate (APS); and D-luciferin and or analogs of either.

As used herein, the terms "fluorophore," "fluorescent moiety," "fluorescent label" and "fluorescent molecule" are interchangeable and refer to a molecule, label or moiety that has the ability to absorb energy from light, transfer this energy internally, and emit this energy as light of a characteristic wavelength.

As used herein, the terms "quencher," "quencher moiety," and "quencher molecule" are interchangeable and refer to a molecule, moiety, or label that is capable of quenching a fluorophore emission. This may occur as a result of the formation of a non-fluorescent complex between the fluorophore and the quencher.

As used herein, the term "FRET labels" refer to fluorophores or quenchers.

As used herein, the terms "quencher-fluorophore pair" and "fluor-quench pair" are interchangeable and refer to a pair of FRET labels including a fluorophore and a quencher that is capable of quenching the fluorophore.

Figure 2:
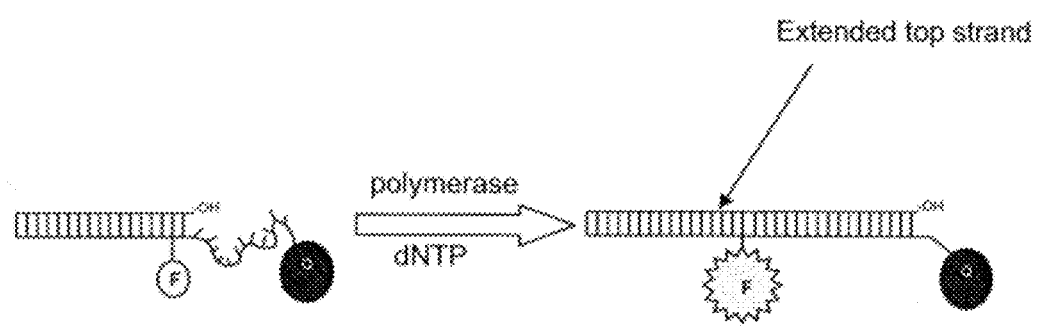
FIG. 2 shows a diagram of an embodiment of the primer-template duplex in a polymerized state (State II).

As used herein, the terms "fluorogenic substrate," "primer-template duplex," "duplex" and "FRET substrate" are interchangeable and refer to a primer-template nucleic acid duplex as shown in FIG. 1 or 2 in which the template (bottom strand in FIG. 1) has a region of hybridization (region A) with the primer (top strand in FIG. 1) and a 5' single-stranded tail. In the presence of a polymerase, the primer-template duplex may be extended into the single-stranded tail (region B). The primer and template may be covalently linked, for example, as a stem-loop structure (see dotted line in FIG. 1). A quencher and a fluorophore are attached to the FRET substrate such that when the substrate is not polymerized, the fluorophore is quenched by the quencher and when the substrate is polymerized, the fluorophore is no longer quenched by the quencher. Thus, one of the FRET labels (quencher or fluorophore) is bound to the 5' single-stranded tail (region B) and one of the FRET primers is bound to region A of FIG. 1 either on the template or the primer, internal to the 3' end of the primer. If the quencher is bound to the 5' single-stranded tail, the fluorophore is bound within region B of FIG. 1 either to the template or to the primer. If the fluorophore is bound to the 5' single-stranded tail, the quencher is bound within region B of FIG. 1 either to the template or to the primer. The distance between the fluorophore and the quencher is chosen to allow the quencher to quench the fluorophore when unpolymerized and to separate the quencher and fluorophore upon polymerization such that fluorescence is emitted. Thus, the distance between the quencher and fluorophore depends upon the specific quencher used and may depend upon the specific quencher-fluorophore pair used. A "primer-template hybrid duplex" is a particular kind of "primer-template duplex" in which the nucleic acid is a hybrid (e.g., DNA:RNA hybrid).

As used herein, the terms "fluorogenic standard" "standard duplex" and "standard," are interchangeable. A standard cannot be used for a substrate because it is already "filled in." Therefore, a standard may be visualized by filling in a primer-template nucleic acid duplex (a fluorogenic substrate) as shown in FIG. 1 or 2. A fluorogenic standard is a complement-template duplex in which a template (bottom strand in FIG. 1) hybridizes with a complement (a "filled in" top strand in FIG. 1).

As used herein, the term "Complement" refers to a sequence that is equivalent to the same sequence that is produced when a polymerase extends the primer to the end of the template, and hence is the complementary sequence to that template. The Complement and template may be covalently linked, for example, as a stem-loop structure (see dotted line in FIG. 1). However, the fluorogenic standard may be created by any method known to the skilled artisan and does not have to be created by filling in a fluorogenic substrate.

As used herein, the term "duplex area" refers to the area of hybridization between the primer and the template (see, for example, region A of FIG. 1).

Methods

In general, the specification provides methods and compositions for assaying for the presence and activity of one or more polymerases in a sample using a non-radioactive method, herein referred to as a FRET polymerase assay. The methods provided herein also have the advantage that the fluorescence change that occurs upon polymerization may be monitored in real-time or as an end-point determination.

The methods provided herein require fewer reagents, have a quicker preparation time, have less dead time, and less read time. In addition, the methods provide the further advantage of being less variable than many of the available non-radioactive methods. The methods provided herein are amendable to many formats, e.g., individual tubes, tube strips, microtiter plates, or solid surfaces (for single molecule detection applications). Fluorescence measurements may be made, for example, using a fluorometer, plate reader with fluorescent detector or a real-time PCR thermocycler.

The methods and compositions provided herein are at least partially based on the use of a fluorogenic substrate. When unpolymerized, the single-stranded tail with the quencher attached may loop back and quench the fluorophore. When polymerized, the tail becomes a part of the duplex and the distance between the fluorophore and quencher is increased to a point at which the quencher can no longer quench the fluorophore. Thus, the methods and compositions provided herein are at least partially based on the ability of a polymerase to polymerize from the primer portion of the substrate thereby increasing the distance between the fluorophore and the quencher such that the fluorophore is no longer quenched. In some embodiments, the fluorophore is attached to the single-stranded tail of the fluorogenic substrate and the quencher is attached to either the primer or the template internally to the single-stranded tail.

Also included herein are methods of detecting nucleic acid polymerase activity by providing a fluorogenic substrate (a primer-template duplex). The fluorogenic substrate has a fluorophore and a quencher attached such that when the fluorogenic substrate is unpolymerized, the quencher can quench the fluorophore and when the fluorogenic substrate is polymerized, the quencher and fluorophore are separated at a distance such that the quencher can no longer quench the fluorophore. In some embodiments, the quencher is attached to the single-stranded tail of the fluorogenic substrate and the fluorophore is either attached to the template internal to the single-stranded tail or attached to the primer. In some embodiments, the fluorophore is attached to the single-stranded tail of the fluorogenic substrate and the quencher is either attached to the template internal to the single-stranded tail or attached to the primer. The methods further include contacting the duplex with at least one polymerase; contacting the duplex with at least one nucleotide triphosphate or analog thereof; and detecting a signal from the fluorophore, wherein a change in the signal compared to a control is indicative of nucleic acid polymerase activity. The methods further include analyzing polymerase mutants using the FRET assay described herein by comparing the results for at least one mutant and non-mutant polymerase and identifying whether the slope of the fluorescence signal is greater for one mutant than for another (or compared to the non-mutant polymerase).

Also included herein are methods of quantifying the amount of a polymerase in a sample using a fluorogenic substrate (i.e., a primer-template duplex) and a fluorogenic standard (i.e., a primer-template duplex that is "filled-in"). The fluorogenic substrate and standard have a fluorophore and a quencher attached. The fluorophore and quencher are separated from each other at a distance such that when the fluorogenic substrate is unpolymerized, the quencher can quench the fluorophore and when the fluorogenic substrate is polymerized, the quencher can no longer quench the fluorophore. In some embodiments, the quencher is attached to the single-stranded tail of the fluorogenic substrate and the fluorophore is either attached to the template internal to the single-stranded tail or attached to the primer. In some embodiments, the fluorophore is attached to the single-stranded tail of the fluorogenic substrate and the quencher is either attached to the template internal to the single-stranded tail or attached to the primer. The methods disclosed herein further include contacting the substrate with at least one polymerase; contacting the substrate with at least one nucleotide triphosphate or analog thereof; and detecting a signal from the fluorophore. The methods further include providing different concentrations of the standard wherein the standard is a "filled-in" version of the substrate. The results from different concentrations of the standard are used to quantitate the activity of the polymerase in units.

In some embodiments, each of the steps of the FRET polymerase assays described herein above is a distinct step. In some embodiments, they may not be distinct steps. In other embodiments, the FRET polymerase assays may not have all of the above steps or may have other steps in addition to or instead of those listed above. The steps of the FRET polymerase assays may be performed in another order. Subsets of the steps listed above as part of FRET polymerase assays may be used to form their own method.

In some embodiments, the methods may be used to identify compounds that modulate nucleic acid polymerase activity. Such methods comprise:

providing a FRET substrate, wherein the FRET substrate is a primer-template duplex comprising a nucleic acid template and a nucleic acid primer, wherein the duplex comprises a single-stranded tail having a 5' end having a quencher attached and wherein the template, or the primer comprises a fluorophore;

contacting the duplex with a nucleic acid polymerase;

contacting the duplex with at least one nucleotide triphosphate or analog thereof;

contacting the duplex with a compound; and detecting a signal from the fluorophore, wherein a change in the signal compared to a control is indicative that the compound modulates nucleic acid polymerase activity. The FRET substrates may be any nucleic acid, including DNA, RNA, mixtures of DNA and RNA, and analogs thereof. The FRET substrate may be used in methods for identifying the presence of at least one polymerase in a sample, quantifying the amount of at least one polymerase in a sample, and identifying modulators of at least one polymerase. In some embodiments, the compounds increase polymerase activity or decrease polymerase activity.

Fluorescent/Fluorogenic Substrates

The methods and compositions of the FRET polymerase assay disclosed herein provide fluorogenic substrates ("substrates") that are used to identify the presence of or measure/quantitate polymerase activity and utilize the principle of fluorescence resonance energy transfer (FRET).

With reference to FIG. 1, the fluorogenic substrate is a primer-template duplex comprising a nucleic acid template and a nucleic acid primer, wherein the duplex comprises a single-stranded tail having a 5' end having a quencher attached and wherein the template or the primer has a fluorophore attached. In the depiction in FIG. 1, "F" and "Q" represent a fluorophore and a non-fluorescent quencher, respectively. In this particular case, the primer and template are formed by a stem-loop sequence and hence may be created from the same oligonucleotide. The primer and template may also be two distinct oligonucleotides (see FIG. 2). As noted in the figure, the single-stranded region is flexible thereby allowing the quencher and fluorophore to come into close proximity. FIG. 2 depicts the conversion of substrate into product and a mechanism that results in an increase in fluorescence as a result of polymerization. In the presence of a polymerase, the primer-template duplex may be extended into the single-stranded tail (region B). The double-stranded region is more rigid and elongated compared to the single-stranded region in the substrate. Formation of the double-stranded form results in a spatial separation of the fluorophore and quencher. Spatial separation results in a reduction of the quenching ability of the quencher moiety and a concomitant increase in fluorescence from the fluorophore.

The fluorogenic substrate may have any nucleic acid composition, including RNA, DNA, and mixtures thereof. As used herein, the terms "fluorogenic substrate," "substrate," "primer-template duplex" and "FRET substrate" are interchangeable and refer to a primer-template nucleic acid duplex as shown in FIG. 1 or 2 in which the template (bottom strand in FIG. 1) has a region of hybridization (region A) with the primer (top strand in FIG. 1) and a 5' single-stranded tail.

A "primer-template hybrid" refers to a particular kind of duplex in which the nucleic acid is a hybrid (e.g., DNA:RNA hybrid). In the presence of a polymerase, the primer-template duplex may be extended into the single stranded tail (region B). The primer and template may be covalently linked for example as a stem-loop structure (see dotted line in FIG. 1). One of the FRET labels (quencher and fluorophore) is bound to the 5' single-stranded tail (region B) and one of the FRET primers is bound to region A of FIG. 1 either on the template or the primer, internal to the 3' end of the primer. If the quencher is bound to the 5' single-stranded tail, the fluorophore is bound within region A of FIG. 1 either to the template or to the primer. If the fluorophore is bound to the 5' single-stranded tail, the quencher is bound within region A of FIG. 1 either to the template or to the primer. The distance between the fluorophore and the quencher is chosen to allow the quencher to quench the fluorophore when unpolymerized and to separate the quencher and fluorophore upon polymerization such that fluorescence is emitted. Thus, the distance between the quencher and fluorophore depends upon the specific quencher used and may depend upon the specific quencher-fluorophore pair used. In some embodiments, the distance between the fluorophore and quencher is between about 3 and 20 nucleotides, including about 4, 5, 6, 7, 8, 9, 10, 11, 12, 13, 14, 15, 16, 17, 18, and 19 nucleotides.

In some embodiments, the primer and template are covalently linked producing a stem-loop structure (see FIG. 1). In some embodiments, the primer and template are not covalently linked (see FIG. 2). In some embodiments, the primer and template are not covalently linked and the substrate is produced by allowing mixtures of the separate primer and template oligonucleotides to anneal. In some embodiments, it may be advantageous for the primer and template to be unlinked for certain methods, such as for quantitation of the activity of a nucleic acid polymerase. For example, when the methods provided herein are used to quantitate the activity of a known polymerase using a standard (as discussed herein), the standard and substrate are labeled more equally when using two separate strands to produce the standard and substrate. This is because, using known methods, the labeling efficiency will be different for a longer strand than for a shorter strand. When making the two strands separately and putting both labels on the template strand, the same template strand may be used to make both the standard and the substrate, allowing for quantitation.

In some embodiments, the primer portion of the fluorogenic substrate may be of any length that is usable in the assay, but is typically between about 3 and 25 nucleotides shorter than the template. In some embodiments, the primer is between about 3 and 50 nucleotides in length, including between about 5 and 25 nucleotides in length, including 6, 7, 8, 9, 10, 11, 12, 13, 14, 15, 16, 17, 18, 19, 20, 21, 22, 23, and 24 nucleotides in length.

In some embodiments, the template part of the fluorogenic substrate may be of any length that is usable in the assay, but is typically between about 3 and 25 nucleotides longer than the primer. In some embodiments, the template is between about 6 and 53 nucleotides in length, including between about 10 and 32 nucleotides in length, including 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 and 52 nucleotides in length.

The fluorophore may be attached to the primer or the template of the substrate. The fluorophore may be any fluorophore known in the art, including, but not limited to those listed herein under the heading "Fluorescent Label." In some embodiments, the fluorophore is located on the primer internally, but not at the 3' end. In some embodiments, the fluorophore is located on the template internally, but not at the 5' end of the double-stranded region. In some embodiments, the fluorophore is located on the template on the 5' single-stranded tail. In some embodiments, the fluorophore is located at the 5' end of the 5' single-stranded tail. In some embodiments, the fluorophore is located at a distance from the quencher such that when the fluorogenic substrate is not polymerized the fluorophore is quenched by the quencher and when the fluorogenic substrate is polymerized the fluorophore is not quenched by the quencher. In some embodiments, the fluorophore is located between about 3 and 25 nucleotides from the quencher, including about 4, 5, 6, 7, 8, 9, 10, 11, 12, 13, 14, 15, 16, 17, 18, 19, 20, 21, 22, 23, and 24 nucleotides from the quencher. In some embodiments, the fluorophore is located internally on the template and the quencher is located at the 5' end of the single-stranded tail. In some embodiments, the fluorophore and quencher are both located on the template. This is advantageous because it allows the production of the template for both the substrate and the standard at the same time, increasing the chance that they will have the same amount of fluorescence.

The quencher may be located on the primer or the template of the substrate. In some embodiments, the quencher is located on the template. The quencher may be any quencher known in the art, including, but not limited to those listed herein under the heading "Quenchers." In some embodiments, the quencher is located on the primer internally, but not at the 3' end. In some embodiments, the quencher is located on the template internally, but not at the 5' end of the double-stranded region. In some embodiments, the quencher is located on the template on the 5' single-stranded tail. In some embodiments, the quencher is located at the 5' end of the 5' single-stranded tail. In some embodiments, the quencher is located at a distance from the fluorophore such that when the fluorogenic substrate is not polymerized the fluorophore is quenched by the quencher and when the fluorogenic substrate is polymerized the fluorophore is not quenched by the quencher. In some embodiments, the quencher is located between about 3 and 25 nucleotides from the fluorophore, including about 4, 5, 6, 7, 8, 9, 10, 11, 12, 13, 14, 15, 16, 17, 18, 19, 20, 21, 22, 23, and 24 nucleotides from the quencher. In some embodiments, the quencher is located at the 5' end of the single-stranded tail. In some embodiments, the quencher and fluorophore are both located on the template and the quencher is located at the 5' end of the single-stranded tail.

The distance between the fluorophore and the quencher involves a number of analyses. Preferably, the quencher is located at a distance from the fluorophore such that when the fluorogenic substrate is not polymerized the fluorophore is quenched by the quencher and when the fluorogenic substrate is polymerized the fluorophore is not quenched by the quencher. However, there is typically a minimum and maximum distance for which this is true. If the distance is chosen to be at the low end of the range, the resulting fluorescent curve may be biphasic. However, if the distance is at the high end of the range, there is more fluorescence and the quencher may not be able to quench the fluorophore.

The fluorogenic substrate and standard may be synthesized in any manner known to the skilled artisan. Depending on whether the top and bottom strand of the fluorogenic substrate or standard is covalently attached, the method of synthesis may differ. For example, if the top and bottom strand of the fluorogenic substrate or standard are not covalently attached, each strand may be synthesized separately to produce the fluorogenic substrate or standard. For example, the primer, template and Complement may be separately produced and mixed to create the desired duplex (a primer and template mixed for a substrate and a Complement and template mixed for a standard). In addition, if the two strands are covalently attached, the fluorogenic substrate or standard may be produced as one long strand. In this case, the fluorogenic substrate or standard is allowed to anneal such that the homologous regions can hybridize to each other. In some embodiments, the primer strand (top strand in FIG. 1) of the fluorogenic substrate is synthesized separately from the template strand (bottom stand in FIG. 1) and the fluorophore and quencher are both on the template strand. In some embodiments, it may be advantageous to have the fluorophore and quencher on the template strand so that the same template strand may be used for both the standard and the substrate. This ensures that the labeling efficiency (which can vary from batch to batch) will be the same for the standard and the substrate.

Fluorescent/Fluorogenic Standard

The methods and compositions of the FRET polymerase assay disclosed herein provide fluorogenic standards that are used to measure or quantitate polymerase activity by titration with the fluorogenic substrate.

FIG. 1 depicts an exemplary fluorogenic substrate which is a primer-template duplex that may serve as a substrate for polymerase activity. In contrast, the fluorogenic standard is a "filled-in" fluorogenic substrate. The fluorogenic standard will have the same composition and label as the fluorogenic substrate. As used herein "fluorogenic standard," and "standard," are interchangeable and refer to a "filled-in" primer-template nucleic acid duplex (a "filled-in" substrate) in which the template (bottom strand in FIG. 1) has a region of hybridization (region A) with the primer (top strand in FIG. 1) and the 5' single-stranded tail is "filled-in" to create a Complement. The phrase "filled-in" is not meant to imply that the only method of making the fluorogenic standard is to fill-in a fluorogenic substrate.

Thus, for a given fluorogenic standard, the placement of the fluorophore and the quencher will be identical to the fluorogenic substrate. Refer to the section entitled "Fluorescent/Fluorogenic Substrate" for more information.

The fluorogenic standard may be synthesized in any manner known in the art. For example, the Complement strand may be synthesized separately from the template strand and then the two strands allowed to anneal to create the standard. In some embodiments, the Complement and template are covalently linked and the standard is synthesized as a long continuous nucleic acid with the looped out region (see dotted line in FIG. 1) in the center and then allowed to anneal to produce a standard. Alternatively, the standard may be produced by filling-in a fluorogenic substrate.

Fluorescent Label

Any fluorescent label or fluorophore may be used without limitation with the methods and compositions provided herein. In some embodiments, the fluorophore may be quenched by a known quencher. In some embodiments, the fluorophore may be easily incorporated internally to an oligonucleotide or may be incorporated at the 5' end of an oligonucleotide primer or template. In some embodiments, the fluorophore is located on the equivalent position on the primer and the Complement. For example, if the fluorophore is on the $5^{th}$ adenine from the 5' end of the template, it is also located on the $5^{th}$ adenine from the 5' end of the Complement. In some embodiments, the fluorophore is a commonly used fluorophore. Fluorophores that are commonly used in FRET include, but are not limited to, fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl) aminonaphthalene-1-sulfonic acid (EDANS). The fluorophore may be any fluorophore known in the art, including, but not limited to: FAM, TET, HEX, Cy3, TMR, ROX, Texas Red®, LC red 640, Cy5, and LC red 705.

Fluorophores for use in the substrate and standard include, but are not limited to, 4-acetamido-4'-isothiocyanatostilbene-2,2' disulfonic acid; acridine and derivatives (e.g., acridine, acridine isothiocyanate); 5-(2'-aminoethyl) aminonaphthalenel-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives (e.g., coumarin, 7-amino-4-methylcoumarin, 7-amino-4-trifluoromethylcoumarin); cyanosine; 4',6-diaminoidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetraimine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives (e.g., eosin, eosin isothiocyanate); erythrosine and derivatives (e.g., erythrosine B, erythrosine isothiocyanate); ethidium; fluorescein and derivatives (e.g., 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate, and QFITC(XRITC); fluorescamine; IR144; IR1446; Malachite Green isothiocyanate; 4-methylumbelliferone; ortho cresolphthalein; nitrotyro sine; pararosaniline; Phenol Red; B-phycoerythrin; o-phthaldialdehyde; pyrene and derivatives (e.g., pyrene, pyrene butyrate, succinimidyl 1-pyrene butyrate); Reactive Red 4 (Cibacron Brilliant Red 3B-A); rhodamine and derivatives (e.g., 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red®); N,N,N',N'-tetramethyl-6-carboxyrhodamine (TAMRA); tetramethyl rhodamine (tetramethyl rhodamine isothiocyanate (TRITC)); riboflavin; rosolic acid; and terbium chelate derivatives.

Fluorophores for use in the methods and compositions provided herein may be obtained commercially, for example, from Biosearch Technologies (Novato, Calif.), Life Technologies (Carlsbad, Calif.), GE Healthcare (Piscataway N.J.), Integrated DNA Technologies (Coralville, Iowa) and Roche Applied Science (Indianapolis, Ind.). In some embodiments, the fluorophore is chosen to be usable with a specific detector, such as a specific spectrophotometric thermal cycler, depending on the light source of the instrument. In some embodiments, the fluorophore is chosen to work well with a specific quencher. In some embodiments, if the assay is designed for the detection of two or more polymerases (multiplex polymerase assays), two or more different fluorophores are chosen with absorption and emission wavelengths that are well separated from each other (i.e., have minimal spectral overlap).

The fluorophore may be located on the primer or template of the substrate. In some embodiments, the fluorophore is located on the primer internally, but not at the 3' end. In some embodiments, the fluorophore is located on the template internally, but not at the 5' end of the double-stranded region. In some embodiments, the fluorophore is located on the template on the 5' single-stranded tail. In some embodiments, the fluorophore is located at the 5' end of the 5' single-stranded tail. In some embodiments, the fluorophore is located at a distance from the quencher such that when the fluorogenic substrate is not polymerized the fluorophore is quenched by the quencher and when the fluorogenic substrate is polymerized the fluorophore is not quenched by the quencher. In some embodiments, the fluorophore is located between about 3 and 25 nucleotides from the quencher, including about 4, 5, 6, 7, 8, 9, 10, 11, 12, 13, 14, 15, 16, 17, 18, 19, 20, 21, 22, 23, and 24 nucleotides from the quencher. In some embodiments, the fluorophore is located internally on the template and the quencher is located at the 5' end of the single-stranded tail.

Quenchers

Any quencher may be used without limitation in the methods and compositions provided herein. The quencher may be located on either the primer (or Complement) or the template. In some embodiments, the quencher is located on the equivalent position on the primer and the Complement. For example, if the quencher is on the $5^{th}$ adenine from the 5' end of the template, it is also located on the $5^{th}$ adenine from the 5' end of the Complement. Any quencher may be used as long as it decreases the fluorescence intensity of the fluorophore that is being used. Quenchers commonly used for FRET include, but are not limited to, Deep Dark Quencher DDQ-I, DABCYL, Eclipse® Dark quencher, Iowa Black® FQ, BHQ-1, QSY-7, BHQ-2, DDQ-II, Iowa Black® RQ, QSY-21, and Black Hole Quencher® BHQ-3. Quenchers for use in the methods and compositions provided herein may be obtained commercially, for example, from Eurogentec (Belgium), Epoch Biosciences (Bothell, Wash.), Biosearch Technologies (Novato Calif.), Integrated DNA Technologies (Coralville, Iowa) and Life Technologies (Carlsbad, Calif.).

The quencher may be located on the primer (or Complement) or template. In some embodiments, the quencher is located on the primer internally, but not at the 3' end. In some embodiments, the quencher is located on the template internally, but not at the 5' end of the double-stranded region. In some embodiments, the quencher is located on the template on the 5' single-stranded tail. In some embodiments, the quencher is located at the 5' end of the 5' single-stranded tail. In some embodiments, the quencher is located at a distance from the fluorophore such that when the fluorogenic substrate is not polymerized the fluorophore is quenched by the quencher and when the fluorogenic substrate is polymerized the fluorophore is not quenched by the quencher. In some embodiments, the quencher is located between about 3 and 25 nucleotides from the fluorophore, including about 4, 5, 6, 7, 8, 9, 10, 11, 12, 13, 14, 15, 16, 17, 18, 19, 20, 21, 22, 23, and 24 nucleotides from the quencher. In some embodiments, the quencher is located at the 5' end of the single-stranded tail. In some embodiments, the quencher and fluorophore are both located on the template and the quencher is located at the 5' end of the single-stranded tail.

Attachment of Fluorophore and Quencher

The fluorophore and quencher may be attached to the substrate (and standard) using any method known to those of skill in the art. As mentioned above, the fluorophore and quencher may be attached to separate strands or to the same strand as long as the fluorophore and the quencher are separated by a distance such that when the duplex is not polymerized the fluorophore is quenched by the quencher and when the duplex is polymerized the fluorophore is not quenched by the quencher. In some embodiments, the quencher may be attached within the strand (primer or template) and the fluorophore attached at the end of the template. Alternatively, the fluorophore may be attached within the strand (primer or template) and the quencher at the end of the template. In some embodiments, the position of the fluorophore or quencher on the primer is the same as the position on the Complement. For example, if a fluorophore is attached to the primer on the 10$^{th}$ nucleotide from the 5' end, it is also attached to the Complement on the 10$^{th}$ nucleotide from the 5' end.

In some embodiments, it is advantageous to have both the fluorophore and quencher on the template strand. For example, in order to have equivalent labeling efficiency between the substrate and the standard, it is advantageous to have both FRET labels on the template. This is because, using the currently available methods, the labeling efficiency may be different from batch to batch. Thus, if both FRET labels are on the template, the template may be used for both the standard and the substrate. In this case, the substrate may be produced, for example, by mixing the template with primers and allowing them to anneal. In the same way, the standard may be produced by mixing the template with Complement and allowing them to anneal.

In some embodiments, the fluorophore is attached within the strand (either the primer or the template). In some cases it will be advantageous for the quencher to be attached at the end of the template and the fluorophore to be attached within either strand. This is because with currently available methods, it is easier to attach the fluorophore within the strand by modifying an internal base during synthesis. Using most current methods, this is more difficult to do with a quencher.

Modifications

Any of the oligonucleotides provided herein (e.g., the primer, the template or the Complement) may be DNA or RNA or chimeric mixtures or derivatives or modified versions thereof, so long as the substrate is still capable of priming the desired polymerization reaction. The oligonucleotide may be modified at the base moiety, sugar moiety, or phosphate backbone, and may include other appending groups or labels, so long as the substrate is still capable of priming the desired polymerization reaction.

For example, the oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N$^2$-carboxypropyl) uracil, (acp3)w, and 2,6-diaminopurine.

In another embodiment, the oligonucleotide comprises at least one modified sugar moiety selected from the group including, but not limited to, arabinose, 2-fluoroarabinose, xylulose, and hexose.

In some embodiments, the oligonucleotide comprises at least one modified phosphate backbone selected from the group including, but not limited to a phosphorothioate, a phosphorodithioate, a phosphoramidothioate, a phosphoramidate, a phosphordiamidate, a methylphosphonate, an alkyl phosphotriester, and a formacetal or analog thereof.

In some embodiments, the oligonucleotides may be modified to more strongly bind to their complementary oligonucleotide. Examples of modifications that may enhance the binding or an RNA or DNA or to its complementary oligonucleotide include, but are not limited to, 2'-O-alkyl modified ribonucleotides, 2'-O-methyl ribonucleotides, 2'-orthoester modifications (including but not limited to 2'-bis (hydroxylethyl), and 2' halogen modifications and locked nucleic acids (LNAs).

Polymerases

As used herein "polymerase" refers to any enzyme having a nucleotide polymerizing activity. Polymerases (including DNA polymerases and RNA polymerases) useful in accordance with the present teachings include, but are not limited to, commercially available or natural DNA-directed DNA polymerases, DNA-directed RNA polymerases, RNA-directed DNA polymerases, and RNA-directed RNA polymerases. Polymerases used in accordance with the invention may be any enzyme that can synthesize a nucleic acid molecule from a nucleic acid template, typically in the 5' to 3' direction. Polymerases may be known or unknown. Further, samples may be used to identify whether a polymerase in present in the sample.

Exemplary DNA polymerases that may be used in the methods, kits and compositions provided herein include, but are not limited to: *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), and mutants, and variants and derivatives thereof. RNA polymerases such as T3, T5 and SP6 and mutants, variants and derivatives thereof may also be used in accordance with the present teachings. Generally, any type I DNA polymerase may be used in accordance with the present teachings although other DNA polymerases may be used including, but not limited to, type III or family A, B, C etc., DNA polymerases.

The nucleic acid polymerases used in the methods, kits and compositions provided herein may be mesophilic or thermophilic. Exemplary mesophilic DNA polymerases include T7 DNA polymerase, T5 DNA polymerase, Klenow fragment DNA polymerase, DNA polymerase III and the like. Exemplary thermostable DNA polymerases nclude Taq, Tne, Tma, Pfu, Tfl, Tth, Stoffel fragment, VENT™ and DEEPVENT™ DNA polymerases, and mutants, variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., Gene 112:29-35 (1992); Lawyer, F. C., et al., PCR Meth. Appl. 2:275-287 (1993); Flaman, J.-M, et al., Nucl. Acids Res. 22(15):3259-3260 (1994)). Examples of DNA polymerases substantially lacking in 3' exonuclease activity include, but are not limited to, Taq, Tne(exo-), Tma(exo-), Pfu(exo-), Pwo(exo-) and Tth DNA polymerases, and mutants, variants and derivatives thereof.

DNA polymerases for use in the present teachings may be obtained commercially, for example, from Life Technologies, Inc. (Rockville, Md.), Pharmacia (Piscataway, N.J.), Sigma (St. Louis, Mo.) and Boehringer Mannheim. Exemplary commercially available DNA polymerases for use in the present invention include, but are not limited to, Tsp DNA polymerase from Life Technologies, Inc.

RNA polymerases for use in the present teachings may be obtained commercially, for example, from Life Technologies, Inc. (Rockville, Md.), Pharmacia (Piscataway, N.J.), Sigma (St. Louis, Mo.) and Boehringer Mannheim.

Enzymes for use in the compositions, methods and kits provided herein include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al., Science 239:487-491 (1988); U.S. Pat. Nos. 4,889,818 and 4,965,188), Tne DNA polymerase (WO 96/10640), Tma DNA polymerase (U.S. Pat. No. 5,374,553) and mutants, fragments, variants or derivatives thereof (see, e.g., commonly owned, co-pending U.S. patent application Ser. Nos. 08/706,702 and 08/706,706, both filed Sep. 9, 1996, which are incorporated by reference herein in their entireties). As will be understood by one of ordinary skill in the art, modified reverse transcriptases and DNA polymerase having RT activity may be obtained by recombinant or genetic engineering techniques that are well-known in the art. Mutant reverse transcriptases or polymerases may, for example, be obtained by mutating the gene or genes encoding the reverse transcriptase or polymerase of interest by site-directed or random mutagenesis. Such mutations may include point mutations, deletion mutations and insertional mutations. Preferably, one or more point mutations (e.g., substitution of one or more amino acids with one or more different amino acids) are used to construct mutant reverse transcriptases or polymerases for use in the teachings. Fragments of reverse transcriptases or polymerases may also be obtained by deletion mutation by recombinant techniques that are well-known in the art, or by enzymatic digestion of the reverse transcriptase(s) or polymerase(s) of interest using any of a number of well-known proteolytic enzymes.

Polymerases for use in the methods, kits and compositions provided herein may be isolated from their natural biological sources. For example, polymerases may be isolated from cellular, fungal, viral or bacterial sources according to standard procedures for isolating and purifying natural proteins that are well-known to one of ordinary skill in the art (see, e.g., Houts, G. E., et al., J. Virol. 29:517 (1979)). In addition, the polymerases may be prepared by recombinant DNA techniques that are familiar to one of ordinary skill in the art (see, e.g., Kotewicz, M. L., et al., Nucl. Acids Res. 16:265 (1988); Soltis, D. A., and Skalka, A. M., Proc. Natl. Acad. Sci. USA 85:3372-3376 (1988)). Furthermore, the polymerases used herein may be part of a biological sample. The sample may include one or more polymerases. The sample can be purified or unpurified. The sample may be a biological sample that has been treated for use in the methods provided herein. Alternatively, if the biological sample does not interfere with the methods provided herein, it may be used untreated (or unpurified).

Some polymerases are processive and some are not. Processivity is a measure of the average number of nucleotides added by a DNA polymerase enzyme per association (or disassociation) with the template. DNA polymerases associated with DNA replication tend to be highly processive, while those associated with DNA repair tend to have low processivity. Thus, PCR enzymes have good processivity. Reverse transcriptases (e.g., MMLV-based) tend to have low processivity, so it is best if the single-stranded tail (the part that needs to be filled-in) is between about 4 and 7 nucleotides in length. A longer single-stranded tail may give a biphasic curve. Thus, the length of the single-stranded region and the distance between the fluorophore and the quencher may be different depending on the processivity of the enzyme (if known). This needs to be balanced with the fact that the greater the distance between the fluorophore and the quencher, the better the fluorescence signal.

Detection

The detection of the signal may be performed using any reagents or instruments that detect a change in fluorescence from a fluorophore. Fluorescent measurements may be made using a fluorometer, plate reader with fluorescent detector or a real-time PCR thermocycler. Examples of spectrophotometric thermal cyclers include, but are not limited to, Applied Biosystems (AB) PRISM® 7000, AB 7300 real-time PCR system, AB 7500 real-time PCR system, AB PRISM® 7900HT, Bio-Rad ICycler IQ™, Cepheid Smart-Cycler® II, Corbett Research Rotor-Gene 3000, Idaho Technologies R.A.P.I.D.™, MJ Research Chromo 4™, Roche Applied Science LightCycler®, Roche Applied Science LightCycler®2.0, Stratagene Mx3000P™, and Stratagene Mx4000™. It should be noted that new instruments are being developed at a rapid rate and any instruments could be used for the methods provided herein.

Enzyme Activity Measurement

The methods and compositions disclosed herein may be used to measure the activity of a known polymerase and have the advantage of giving the activity in units. In some embodiments, the method for identifying the activity of the enzyme involves the use of a standard and a substrate. In some embodiments, the primer and template for the standard and substrate are not covalently linked. This allows for an equal labeling efficiency between the standard and substrate and may give more accurate quantitation for the enzyme activity. In some embodiments, the method involves generating a standard curve by titrating in the standard and converting the resulting fluorescence to nmol of product.

Kits

Some embodiments provide kits for the quantification or detection of one or more polymerases in a sample, including a fluorogenic substrate. The fluorogenic substrate includes a fluorophore and a quencher, such that the quencher and fluorophore are separated at a distance that when the duplex is not polymerized the fluorophore is quenched by the quencher and when the duplex is polymerized the fluorophore is not quenched by the quencher. The kit may be used in the methods of polymerase activity detection and quantification provided herein. In some embodiments, the kit also includes a standard. In some embodiments, the kits also include a control polymerase (i.e., at a known concentration (in units)). In some embodiments the kits are used for multiplexed reactions, such as to identify one or more polymerases in a sample.

In some embodiments, the kit comprises a multi-well format, such as a 96-well plate. Such plates may be used for analysis of multiple samples including control enzymes and multiple concentrations of the standard duplex for the generation of a standard curve.

Samples

The methods and compositions provided herein may be used for detection and quantification of a polymerase in a sample. The sample may include one or more polymerases. The sample may include purified or unpurified DNA polymerases from viruses, bacteria, fungi, archaea, eukaryotic cells or tissues. The sample may be a biological sample that has been treated to use in the methods provided herein. In some embodiments, if the biological sample does not interfere with the methods provided herein, it can be used untreated (or unpurified).

Inhibitors/Activators

The methods provided herein may also be used for screening for compounds that modulate nucleic acid polymerase activity. When characterizing the effect of inhibitors on a polymerase, the inhibitor is usually added to the substrate mixture. Alternatively, the inhibitor may be pre-incubated with the polymerase by adding it to enzyme/FRET substrate mixture prior to initiating the reaction with the substrate mixture. Examples of inhibitors include, but are not limited to, humic acid, phenols, polyphenols, salts including KCl, NaCl, $CaCl_2$, $BaCl_2$, $AuSO_4$, $AlCl_3$, and the like, naturally occurring and recombinant proteins or nucleic acids, such as anti-Taq antibodies, anti-Phusion affibodies (See Wikipedia.org/wiki/Affibody, version of Aug. 15, 2011) and aptamers for Taq DNA polymerase (Ikebukuro and Noma, Nucl. Acids Res. Suppl. No. 3, 309-310 (2003)).

EXAMPLES

The following examples provide methods and compositions for the FRET polymerase assays provided herein. The FRET polymerase assay methods were partially based on the discovery that when a fluorogenic substrate labeled with a fluorophore and a quencher tail was used, the extension by a polymerase released fluorescence. Without being bound by a specific theory, it is thought that the extension forces the fluor-quench pair apart. The increase in fluorescence increased with the amount of extension of the fluorogenic substrate in a direct relationship, providing a new method for quantifying polymerase activity in a sample. Some exemplary substrate sequences are shown in Table 1. These are substrate sequences that were successfully used in assays to identify the concentration (units) of Taq polymerase activity. However, the assay will work with essentially any sequences as long as the sequences are produced in a substrate format as described herein. In Table 1, the bolded "T" represents the location where the fluorophore is attached. The third column shows the hairpin format. Therefore, the top "T" and bottom "A" are part of the hairpin structure.

TABLE 1

Substrate sequences

| Name | Sequence | Format of the Sequence (Hairpin) |
|---|---|---|
| Polsub-15 | IBK-ATCATATCATCAAC(FAM-dT)GGCCGTCGTT TTACATATGTAAAACGACGGCCAG TT (SEQ ID NO: 4) | T<br>A  GTAAAACGACGGCCAGTT<br>T  CATTTTGCTGCCGGTCAACTACTATACTA-(IBK)<br>A      \\(FAM) |
| Polsub-16 | /56-TAMN/ ATCATATCATCAAC/iFluorT/G GCCGTCGTTTTACATATGTAAAAC GACGGCCAGTT (SEQ ID NO: 5) | T<br>A GTAAAACGACGGCCAGTT<br>T CATTTTGCTGCCGGTCAACTACTATACTA-(TAM)<br>A      \\(FAM) |
| Polsub-15(Cy3) | BHQ-ATCATATCATCAAC(Cy3 dT)GGCCGTCGTTTTACA TATGTAAAACGACGGCCAGTT (SEQ ID NO: 6) | T<br>A GTAAAACGACGGCCAGTT<br>T CATTTTGCTGCCGGTCAACTACTATACTA-(BHQ)<br>A      \\(Cy3) |
| Polsub-15Cmm | IBK-TCATATCATCCAC(FAM-dT)GGCCGTCGTTTTACATA TGTAAAACGACGGCCAGTC (SEQ ID NO: 7) | T<br>A  GTAAAACGACGGCCAGTC<br>T  CATTTTGCTGCCGGTCACCTACTATAACT-IBK<br>A      \\(FAM) |
| Polsub-15PAP | IBK-ATCATATCATCGAC(FAM-dT)GGCCGTCGTTTTACATATGTA AAACGACGGCCAGT(ddC) (SEQ ID NO: 8) | T<br>A GTAAAACGACGGCCAGT(ddC)<br>T CATTTTGCTGCCGGTCAGCTACTATACTA-IBK<br>A      \\(FAM) |
| Polsub-15PAPmm | IBK-ATCATATCATCCAC(FAM-dT)GGCCGTCGTTTTACATATGTA | A GTAAAACGACGGCCAGT(ddC) |

TABLE 1-continued

Substrate sequences

| Name | Sequence | Format of the Sequence (Hairpin) |
|---|---|---|
| | AAACGACGGCCAGT(ddC) (SEQ ID NO: 9) | T CATTTTGCTGCCGGTCACCTACTATACT-IBK<br>A  \ (FAM) |
| STV(for reverse transcriptase) | 5'(BHQ1)aucaucauaucaucaa cuggccgucguuuuacATATGTAA AACGACGGCCAG(dT-FAM)T-3' (SEQ ID NO: 10) | T (FAM)\<br>A  GTAAAACGACGGCCAGTT<br>T  r(cattttgcagccggtcaacuacuauacua)\<br>A  BHQ1 |

Materials and Methods

The following methods were used for all of the experiments detailed below in the Examples except as otherwise noted.

Oligonucleotide Sequences—Synthesis and Modification

The oligonucleotides were chemically synthesized using standard phosphoramidite-based nucleoside monomers and established solid phase oligomerization cycles according to Beaucage, S. L. and Iyer, R. P. (*Tetrahedron*, 1993 (49) 6123; *Tetrahedron*, 1992 (48) 2223). RNA phosphoramidites were protected with 2'O-TBDMS groups. Synthesis of oligonucleotides was performed on a BioAutomation Mer-Made 192 or BioAutomation MerMade 12 synthesizers (BioAutomation Corp, Plano, Tex.). Eight equivalents of activator were used for every equivalent of phosphoramidite to provide a satisfactory stepwise coupling yield of >98% per base addition. Purification of the individual oligonucleotides for in vitro screening was carried out using high throughput desalting and alcohol precipitation techniques. Analytical HPLC (ion exchange or reverse-phase) was used for determining single strand purity, MALDI mass spectrometry was used for determining oligonucleotide identity, and UV spectroscopy was used for quantitative determination of inhibitors.

Preparation of the Reaction and Standard Formulations

The Reaction Formulation contained the polymerase substrates (nucleic acid template, primer, and deoxyribonucleoside triphosphates (dNTPs)), buffer salts and divalent cation (typically magnesium or manganese). The template and primer may be DNA or RNA, or a hybrid formed between the two forms of nucleic acid. The template and primer may also be created from a single oligonucleotide containing a stem-loop structure. Polymerase was added to this formulation (except for the no enzyme control) to start the reaction at time zero. Alternatively, dNTPs or other reaction components could be used to start the reaction.

The Standard Formulation contained the same template used in the Reaction Formulation. The Standard Formulation also included all of the other components used in the Reaction formulation except enzyme. In addition, the Standard formulation included, at various known concentrations, an oligonucleotide referred to as "Complement." Complement was equivalent to the same sequence that was produced when a polymerase extended the primer to the end of the template, and hence was the complementary sequence to that template. A dilution series of Complement was created in the Standard Formulation. The primer concentration was sequentially reduced at the same rate that the Complement concentration was increased such that the total concentration of primer plus Complement always equaled the primer concentration in the Reaction formulation. The Standard Formulations containing known concentrations of Complement were used to create a standard curve in which the fluorescence signal was plotted against the concentration of the Complement. Since the Complement represents the product formed by polymerization in the Reaction Formulation, the standard curve was used to convert the amount of fluorescence signal generated in the polymerase reaction into moles of product.

Standard curves produced using this approach do not need to be used if only a relative measure of polymerase activity is needed. For example, to assess the relative effect of mutations or to evaluate the effects of stimulatory or inhibitory molecules on polymerase activity, the standard curve may not be required.

Detection of Polymerase Activity—

The polymerase reaction was started by addition of polymerase (or other required substrate or cofactor) to the Reaction Formulation. FIGS. 1 and 2 depict the structure of a typical template with annealed primer. The single-stranded region of the template, due to the fact that it is single-stranded, is highly disordered and flexible. This flexibility allows the quencher to come into close proximity to the fluorophore, effectively quenching the fluorescence of the fluorophore. As nucleotides are incorporated by the polymerase, the stretch of single-stranded nucleic acid is converted to double-stranded nucleic acid. Double-stranded nucleic acid is more rigid and has less degree of freedom than single-stranded nucleic acid. Hence, the incorporation of nucleotides by a polymerase results in spatial separation of the quencher and fluorophore compared to the starting substrate. Spatial separation of these moieties results in a decrease in quenching and a corresponding increase in the fluorescent signal.

This assay is amendable to many formats, e.g., individual tubes, tube strips, microtiter plates, or solid surfaces (for single molecule detection applications). The fluorescence change that occurs upon polymerization may be monitored in real time or as an end-point determination. Fluorescence measurements may be made using a fluorometer, plate reader with fluorescence detector or a real-time PCR thermocycler.

Calculations

Typical Unit definition: One unit is equivalent to the amount of enzyme required to incorporate 10 nmoles of nucleotide into double stranded nucleic acid in 30 minutes. The activity per microliter of enzyme is calculated from the following equation:

$$\text{Activity}(U/\mu l) = \frac{\text{activity slope }(RFU/\text{min}/\mu l)}{\text{standard slope }(RFU/nM)} \times$$

$$\frac{100 \times 10^{-6}}{\text{reaction}} \frac{1}{\text{}} \times \frac{15 \text{ bases}}{\text{moleproduct}} \times 30 \text{ minutes} \times \frac{1 \text{ Unit}}{10 \text{ nmoles}}$$

Example 1: Duplex Energy Transfer Substrate 1 nM Taq Serial Dilution to 1 pM Taq The FRET polymerase assays were performed with the substrate having the primer (SEQ ID NO:1) and template (SEQ ID NO:2) shown below. The FRET substrate (and standard) included the fluorophore FluorT and the quencher BHQ1 (see template SEQ ID NO:2). The standard used was a "filled in" version of the substrate using the Complement sequence shown below (SEQ ID NO:3) and the template (SEQ ID NO:2). The FRET polymerase assay was performed in real-time over 40 minutes with Taq polymerase diluted from 1 nM to 1 pM. The concentrations of the Reaction Formulation components used were 300 nM Substrate; 500 mM dNTPs; 25 mM TAPS, pH 9.35; 50 mM KCl; and 5.0 mM $MgCl_2$. The reaction was optimized for Taq polymerase. Other polymerases may have different optima.

```
Primer:
                                           (SEQ ID NO: 1)
5' CGTAGGACTCGGAAGTCGAC3'

Template:
                                           (SEQ ID NO: 2)
5'/BHQ1/CAGCGTGGGGTTTGCG/FluorT/

CGACTTCCGAGTCCTACG 3'

Complement:
                                           (SEQ ID NO: 3)
5' CGTAGGACTCGGAAGTCGACGCAAACCCCACGCTG 3'
```

Figure 3:
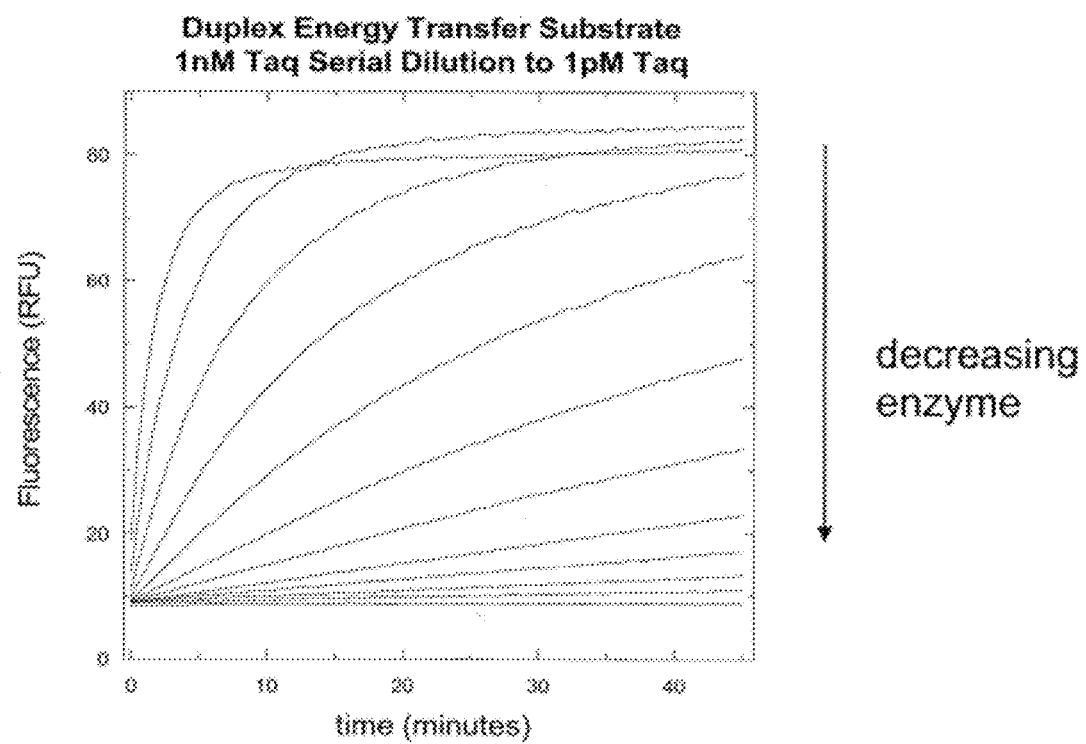
FIG. 3 is a graph showing the fluorescence (Relative Fluorescence Unit (RFU)) of FRET substrate over time using varying amounts of Taq polymerase (from 1 nM to 1 pM).

The relationship of fluorescence (RFU) with time is shown in FIG. 3. The results showed the increase that occurs as polymerase converted substrate into product. The y axis represents the fluorescence signal and the x-axis represents the time after polymerization was started. By re-plotting the initial rates of fluorescence increase versus the amount of enzyme added to each reaction, it is possible to generate an enzyme activity slope. This slope may then be used in the activity calculation described in the materials and methods part of the Example. The units of Taq activity (or another polymerase) may be measured in this way.

Example 2: Finding the Concentration (Units) of an Enzyme

The FRET polymerase activity assay was used to quantify the activity of DNA-dependent polymerases as follows. The assay employed a 35-mer template oligonucleotide that was modified on its 5' end with a quenching molecule and contained an internal fluorescein label (SEQ ID NO:2). Annealing of a 20-mer oligonucleotide to the 35-mer template generated the primed-template referred to as the 'substrate duplex' (SEQ ID NO:1 and SEQ ID NO:2). Extension of the 'substrate duplex' by the polymerase positioned the quencher away from the fluorescein residue resulting in an approximate 15-fold fluorescence enhancement from the internal fluorescein label. A 'standard duplex' oligonucleotide was made with the same modified 35-mer template annealed with its complete Complement representing the full product of the extension reaction (Complement; SEQ ID NO:3).

The FRET polymerase assay was performed under steady state conditions with excess 'substrate duplex' and limiting polymerase. The assay was performed in a 96-well format at 60° C. in an ABI 7900 Real-Time PCR instrument (Life Technologies, Foster City, Calif.). The kinetic extension reaction was monitored for 99 isothermal cycles of 30 seconds each, approximately 65 minutes. The 96-well format allowed for the analysis of six samples, three dilutions of the enzyme to be tested and three dilutions of a control enzyme. The samples were diluted 2400-fold and then a five point dilution series was made of each sample. Each dilution series was analyzed in duplicate. Thus the enzyme and the control samples were analyzed six times. The last two rows of the 96-well assay plate contained the 'standard duplex' at 8 different known concentrations for the standard curve. Pre-made reactions strips and standard strips make assembly of the reaction plates easy.

Calculating the slopes of the kinetic extension reactions and comparing them to the slope of the standard curve allowed determination of the enzyme activity in Unit/µL. Calculations used are presented below.

Procedure: Fret Polymerase Assay for DNA Polymerases

The protocol was composed of four parts: 1) enzyme dilution, 2) reaction plate set-up, 3) isothermal polymerase reaction using ABI 7900 Real-Time PCR machine, and 4) data analysis.

For the enzyme dilution, the test and control enzymes (5 U/µl or 500 nM) were first diluted 2400-fold in triplicate using enzyme dilution buffer, giving a total of six samples to test. A five-step 'dilution series' was made from each of the six samples. The 'dilution series' were made in three 12-tube strips. This simplified the addition of the enzyme to the reaction strips.

For the set-up of the 96-well reaction plate, 5 µl of enzyme from the three dilution strips was added to three reaction strips. After mixing, two 20 µl aliquots were removed from the each reaction strip and added to the plate to rows A through F. 20 µl from the standard strip was added to rows G and H.

Calculation: FRET Polymerase Assay, Enzyme Dilution

The FRET polymerase assay was performed under steady state conditions with the enzyme as the limiting factor. Polymerases labeled at 5 U/µL or at a concentration of approximately 500 nM were diluted 2400-fold. The enzymes could be in storage buffer containing 50% glycerol. The plate layout could measure six samples. There was flexibility in the arrangement of the samples. For example, one could test five different enzymes and one control or one enzyme and one control with three replicate dilutions each. Enzymes were diluted in Enzyme Dilution Buffer (EDB). The dilution scheme was as follows: 5 µL of the stock enzyme (5 U/µL or 500 nM) was diluted 20-fold (dilution A). Dilution A was further diluted two times (B and C) resulting in a 2400-fold dilution, Dilution C. Dilution C was used to make the dilution series. The dilutions series was made in three 12-tube strips for ease of aliquoting into the reactions strips.

Initial dilution: Six sets of three tubes were set up on ice. The tubes were labeled using numbers to refer to the enzyme sample and letters to refer to a specific dilution, for example: Enzyme Dilution A=e1A and Control Dilution A=c1A. Enzyme Dilution Buffer (EDB) was added to the tubes as follows: tube marked A, add 95 µL of EDB; tubes marked B, add 290 µL of EDB; tubes marked C, add 750 µL of EDB. Addition of Enzyme: 5 µL of enzyme were added, using an L-10 pipetor to tube 1A. The tip was carefully wiped with a Kimwipe®. Using a larger pipettor, set at ~50 µL, the sample was mixed by pipetting up and down 10 times. In general, this sample was in 50% glycerol so care was taken to ensure it was well mixed. 10 µL was removed from tube 1A to tube 1B and pipetted up and down to rinse the tip. The sample was mixed by pipetting up and down about 10 times as described above. 250 µL was removed from tube 1B to tube 1C and pipetted up about 10 times to rinse the tip and to mix the sample. Enzyme was added to tubes by dispensing ~200 µL of each of the dilutions C to tubes.

The calculations used were based on the following definition of unit activity of Taq DNA polymerase: One unit of enzyme is defined as the amount that can incorporate 10 nmoles of dNTPs into acid insoluble material per 30 minutes in a 10 minute incubation at 74° C. under the following conditions: 25 mM TAPS, pH 9.3 (Room Temp; 50 mM KCl; 2 mM $Mg_2Cl_2$; 1 mM β-mercaptoethanol; 200 µM each dATP, dGTP, dTTP; 100 µM [α-$^{32}$P] dCTP (0.05-0.1 Ci/mmol); 'Activated' salmon sperm DNA was used as a substrate. The following formulae were used:

$$\text{Activity }(U/\mu l) = \frac{\text{Activity slope }(RFU/\text{min}/\mu L)}{\text{Standard Slope }(RFU/nM)} \times$$

$$\frac{50 \times 10^{-6} \text{ L}}{\text{reaction}} \times \frac{15 \text{ bases}}{\text{mole product}} \times 30 \text{ minutes} \times \frac{1 \text{ Unit}}{10 \text{ nmoles}}$$

$$\text{Activity }(U/\mu l) = \frac{\text{Activity slope }(RFU/\text{min}/\mu L)}{\text{Standard Slope }(RFU/nM)} \times .00225 \times \text{``FACTOR''}$$

Activity slope: RFU/min=Rate of the reaction=Slope of the line of the RFU vs time. "µL" was determined as follows: 1 µl was divided by the final dilution factor (2400); multiplied by the "effective" amount of enzyme added to the reaction.

Figure 4:
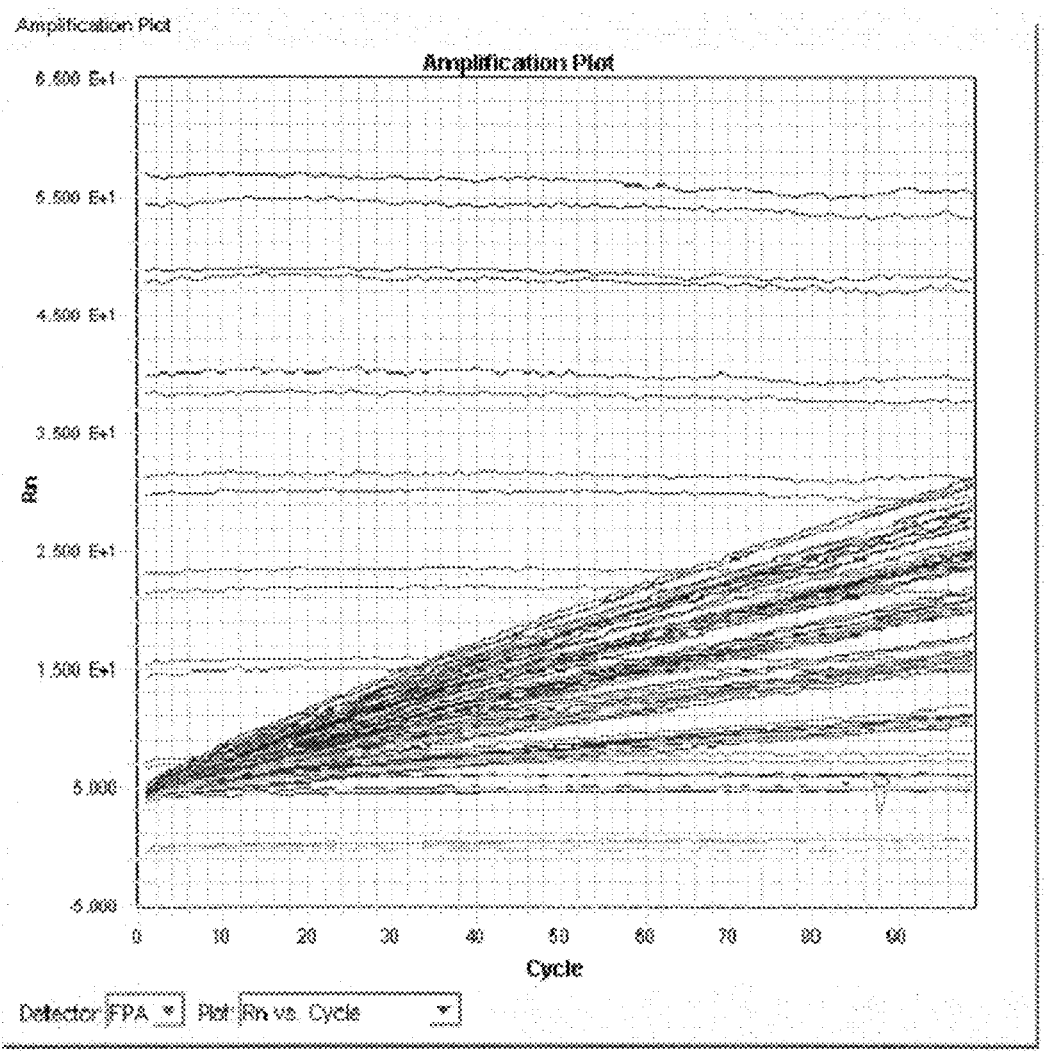
FIG. 4 is a fluorescence signal plot for standards and enzyme reactions.

FIG. 4 shows the fluorescence signal plots for the Standards and enzyme reactions. The horizontal lines represent the fluorescence signals of the standards, run in duplicate. As the amount of Complement was increased, the fluorescence signal increased proportionally. The signal from each Standard remained constant over the time course of the measurement because the concentration of Complement and template did not change. Furthermore, since the concentration of Complement was known for each trace, a standard curve could be generated by plotting the fluorescence signal vs. the concentration of Complement. The slope of this curve was used in the activity calculation as described in the Material and Methods section.

Figure 5:
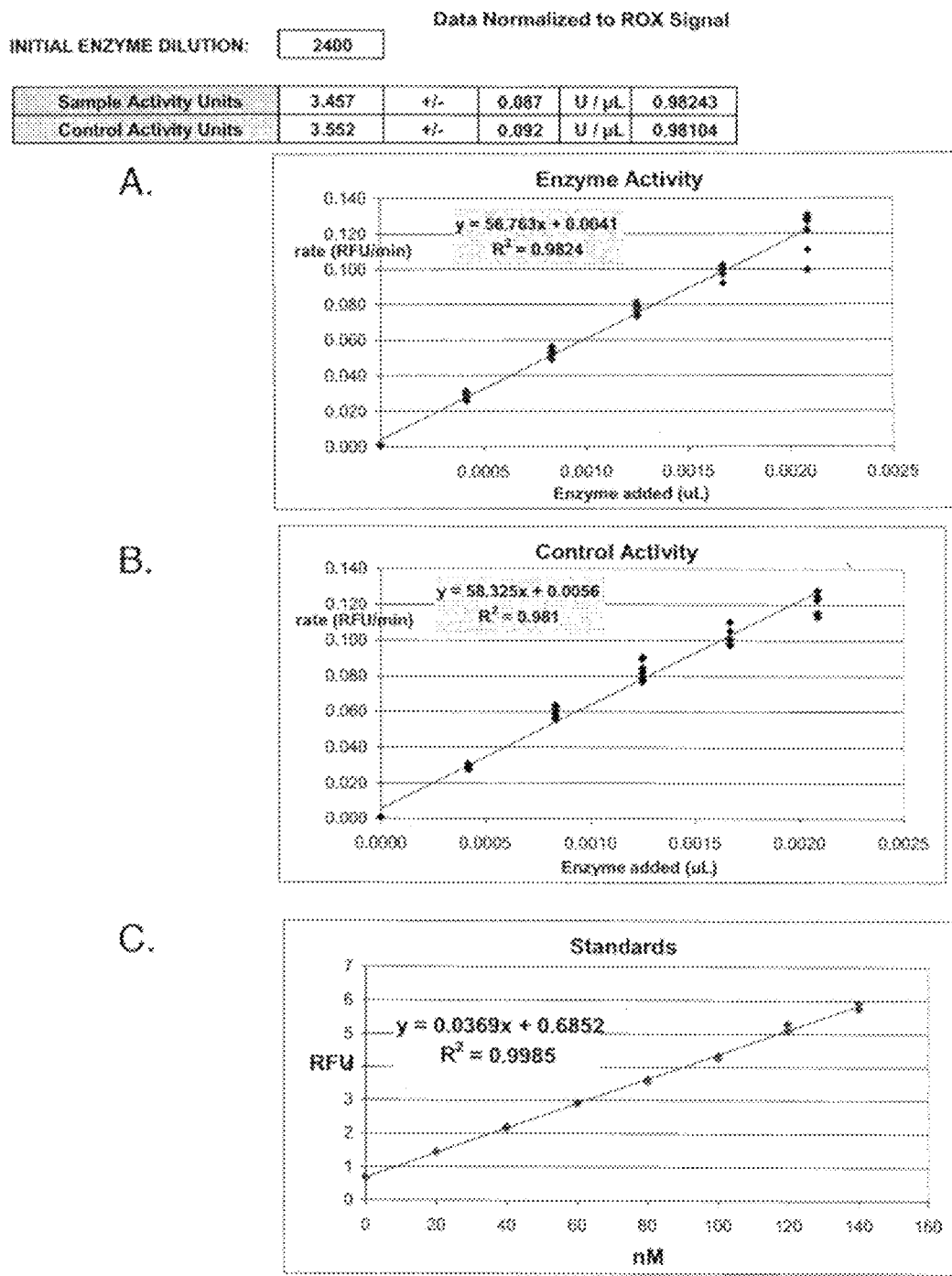
FIGS. 5A-C show various curves generated from fluorescent data depicted in FIG. 4.

FIGS. 5B and 5C represent the fluorescent signal generated in the FRET polymerase reaction. The different lines represent different levels of input enzyme. Since the polymerase product increased in concentration over time, the fluorescence signal increased proportionally. By plotting the initial rate of fluorescence increase vs. the amount of enzyme added to the reaction, an enzyme reaction curve was generated. The slope of this curve was used in the activity calculation.

FIGS. 5A-C represent the curves generated from the fluorescence data above. The top graph (FIG. 5A) represents the curve generated by plotting the initial rate of fluorescence increase vs. the amount of enzyme added to the reaction. The middle graph (FIG. 5B) represents the same plot for the control enzyme, which was used to validate that the assay was working properly. The bottom graph (FIG. 5C) was created by plotting the fluorescence signal (relative fluorescence unit or RFU) vs. the concentration of Complement. The slope of the enzyme activity was divided by the standard slope to determine the polymerase activity in units/W. Alternatively, units/mg of polymerase may be determined by plotting the amount of enzyme added in milligrams instead of microliters.

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

The invention claimed is:

1. A method of quantitating nucleic acid polymerase activity, the method comprising:
   a) providing a test formulation comprising a substrate comprising a primer-template duplex comprising a nucleic acid template and a nucleic acid primer, wherein the template comprises a region of hybridization with the primer and a single stranded tail having a 5' end having a first FRET label attached, and wherein the template comprises a second FRET label within the region of hybridization, wherein one FRET label is a quencher and the other FRET label is a fluorophore;
   b) providing a series of standard formulations comprising increasing concentrations of a standard oligonucleotide and decreasing concentrations of the substrate wherein:
      i) the total concentration of standard oligonucleotide and substrate in each standard formulation equals the primer concentration in step (a);
      ii) the standard oligonucleotide comprises a "filled-in" version of the substrate; and
      iii) each of the standard formulations has no polymerase;
   c) contacting the duplex with a nucleic acid polymerase;
   d) contacting the duplex with at least one nucleotide triphosphate or analog thereof;
   e) detecting a fluorescent signal from the test formulation;
   f) detecting fluorescent signals from each of the standard formulations; and
   g) using the signals obtained from the series of standard formulations and the signal obtained from the test formulation to quantitate the activity of the polymerase in units.

2. The method of claim 1, wherein the primer and template are not covalently linked.

3. The method of claim 1, wherein the primer-template duplex is a primer-template DNA/RNA hybrid duplex.

4. The method of claim 1, further comprising the steps of: comparing the activity results obtained with the nucleic acid polymerase to activity results obtained using a control polymerase; wherein a change in the signal compared to the control is indicative of nucleic acid polymerase activity.

5. The method of claim 1, wherein the fluorophore is selected from the family of fluorescein dyes and the family of rhodamine dyes.

6. The method of claim 1, wherein the second FRET label is not located at the 5' end of the region of hybridization.

7. A method of quantitating nucleic acid polymerase activity, the method comprising:
   a) providing a primer-template duplex comprising a nucleic acid template and a nucleic acid primer, wherein the template comprises a single-stranded tail having a 5' end having a first FRET label attached and the template further comprises a second FRET label within the duplex region of the primer-template duplex, wherein one FRET label is a quencher and the other FRET label is a fluorophore;
   b) contacting the duplex with a nucleic acid polymerase;
   c) contacting the duplex with at least one nucleotide triphosphate or analog thereof;
   d) detecting a signal from the fluorophore;
   e) providing a standard, the standard comprising the primer-template duplex having a "filled-in" single stranded tail;
   f) detecting a signal from the fluorophore; and
   g) using the signal obtained at different concentrations of the standard and the signal obtained from the primer-template hybrid to quantitate the activity of the polymerase in units.

8. The method of claim 7, wherein the first FRET label is a quencher and the second FRET label is a fluorophore.

9. The method of claim 7, wherein the first FRET label is a fluorophore and the second FRET label is a quencher.

10. The method of claim 7, wherein the primer and template are covalently connected.

11. The method of claim 10, wherein the primer and template are covalently connected as a stem-loop structure.

12. The method of claim 7, wherein the quencher and fluorophore are separated from each other at a distance such that when the duplex is not polymerized the fluorophore is quenched by the quencher and when polymerized the fluorophore is not quenched by the quencher.

13. The method of claim 12, wherein the distance is between about 4 and 20 bases.

14. The method of claim 12, wherein the quencher is separated from the fluorophore by about 15 bases.

15. The method of claim 12, wherein the quencher is a DABCYL quencher and the distance is about 5 bases.

16. The method of claim 7, wherein the quencher is a DABCYL quencher.

17. The method of claim 7, wherein the fluorophore is selected from the group consisting of fluorescein, 5-carboxyfluorescein, 2'7'-dimethoxy-4'5'-dichloro-6-carboxyfluorescein, rhodamine, 6-carboxyrhodamine (R6G), N,N,N',N'-tetramethyl-6-carboxyrhodamine, 6-carboxy-X-rhodamine, 4-acetamido-4'-isothiocyanato-stilbene-2,2' disulfonic acid, acridine, acridine isothiocyanate, 5-(2'-aminoethyl)amino-naphthalene1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide; anthranilamide, Brilliant Yellow, coumarin, 7-amino-4-methylcoumarin, 7-amino-4-trifluoromethylcoumarin, cyanosine, 4',6-diaminoidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, diethylenetraimine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-dimethylaminophenylazophenyl-4'-isothiocyanate (DABITC), eosin, eosin isothiocyanate, erythrosine, erythrosine B, erythrosine isothiocyanate, ethidium, 5-(4,6-dichlorotriazin-2-yl)aminofluorescein (DTAF), fluorescein, fluorescein isothiocyanate, QFITC (XRITC), fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene, pyrene butyrate, succinimidyl 1-pyrene butyrate, Reactive Red 4 (Cibacron Brilliant Red 3B-A), lissamine rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101, tetramethyl rhodamine, tetramethyl rhodamine isothiocyanate (TRITC), riboflavin, rosolic acid, and terbium chelate derivatives.

18. The method of claim 7, wherein the detection is using a real-time PCR instrument.

19. The method of claim 7, wherein the polymerase is a DNA polymerase and wherein the DNA polymerase is a DNA-directed DNA polymerase or an RNA-directed DNA polymerase.

20. The method of claim 7, wherein the polymerase is an RNA polymerase, wherein the RNA polymerase is an RNA-directed RNA polymerase or a DNA-directed RNA polymerase.

21. The method of claim 7, wherein the fluorophore is selected from the family of fluorescein dyes and the family of rhodamine dyes.

22. The method of claim 7, wherein the second FRET label is not located at the 5' end of the duplex region.

* * * * *